(12) United States Patent
Fenley

(10) Patent No.: US 7,634,998 B1
(45) Date of Patent: Dec. 22, 2009

(54) HME SHUTTLE SYSTEM

(76) Inventor: Robert C. Fenley, 2534 Central Dr., No. 115, Bedford, TX (US) 76201

( * ) Notice: Subject to any disclaimer, the term of this patent is extended or adjusted under 35 U.S.C. 154(b) by 697 days.

(21) Appl. No.: 11/487,289

(22) Filed: Jul. 13, 2006

Related U.S. Application Data

(60) Provisional application No. 60/699,778, filed on Jul. 15, 2005.

(51) Int. Cl.
A62B 18/08 (2006.01)
(52) U.S. Cl. ............... 128/201.13; 128/200.24; 128/207.16; 128/200.14; 128/909
(58) Field of Classification Search ............ 128/201.13, 128/203.26, 203.27, 204.17, 205.24, 205.12, 128/911, 205.27, 205.28, 205.29, 200.24, 128/207.16, 200.14, 909; 96/108; 55/309, 55/385.1, 478, 481; 95/273
See application file for complete search history.

(56) References Cited

U.S. PATENT DOCUMENTS

| | | | |
|---|---|---|---|
| 5,505,768 A | * | 4/1996 | Altadonna .............. 96/108 |
| 6,550,476 B1 | * | 4/2003 | Ryder .................. 128/201.13 |
| 6,588,421 B1 | | 7/2003 | Diehl et al. |
| 6,792,946 B1 | * | 9/2004 | Waldo et al. .......... 128/205.12 |
| 7,069,928 B1 | * | 7/2006 | Waldo et al. .......... 128/201.13 |
| 7,347,203 B2 | * | 3/2008 | Marler et al. .......... 128/201.13 |

* cited by examiner

*Primary Examiner*—Justine R Yu
*Assistant Examiner*—Christopher Blizzard
(74) *Attorney, Agent, or Firm*—Handley Law Firm, PLLC

(57) ABSTRACT

An HME Filter is provided having with an integral housing having minimal components which eliminating components at the circuit "Y" connector. A closed circuit gas flow is maintained whether an internal filter material is or is not engaged, and with or without a nebulizer aerosolizing medications. The HME SHUTTLE continues to maintain the same closed circuit gas flow during the HME filter materials insertion into the HME SHUTTLE, throughout the course of the HME filter's use in the closed gas flow circuit and during the HME filter materials removal from the HME SHUTTLE. The placement for optimal patient care is to be located between the connection of inhalation and exhalation sides of mechanical ventilator circuit and endotracheal tube of an intubated patient. The HME SHUTTLE also accommodates the docking port for the use of an external nebulizer.

4 Claims, 8 Drawing Sheets

HME SHUTTLE SYSTEM

CROSS-REFERENCE TO RELATED APPLICATION

The present application claims priority to and is a continuation in part of U.S. Provisional Application Ser. No. 60/699,778, filed Jul. 15, 2005, entitled HME Shuttle System, invented by Robert C. Fenley.

TECHNICAL FIELD OF THE INVENTION

The present invention relates in general to mechanical ventilators for medical use, and in particular to heat moisture exchange filters.

BACKGROUND OF THE INVENTION

Adequate humidification of oxygen to a person's lungs has long been recognized as an essential component for maintenance of a healthy pulmonary system. In a healthy individual, traditionally, this is accomplished by an integral relationship between a person's upper airways in general and multiple functions of nasal pathways in particular. For those individuals where their medical conditions require some form of assistance from artificial respiration provided by a mechanical ventilation device, these biological structures used for proper humidification are bypassed.

These mechanical ventilators have used a closed circuit approach where, traditionally, sterile water is heated to a vapor phase and introduced into a medical gas flow delivered to the patient. Recently, a more natural approach has been employed that uses a filter to mimic those natural properties found associated with the human nose. Those filters are called HME (Heat Moisture Exchanger) filters.

The positive physiological properties associated with using HME filters are well-documented. Yet, inherent drawbacks (i.e. breaking the closed gas flow circuit while using an HME filter) remain in their delivery system that still prevent them from achieving their maximum potential. Integrating the use of an HME SHUTTLE, with an internal HME filter; modified and created specifically to fit inside an HME SHUTTLE, will solve these problems. In so doing, a patient will be provided with the optimal airway humidification needed for health.

SUMMARY OF THE INVENTION

An HME SHUTTLE SYSTEM is any device created specifically to maintain a closed circuit gas flow while functioning fully independent of an internal HME (Heat Moisture Exchanger) filter, or concurrently with an internal HME filter designed for this device. For the remainder of this discussion, the HME SHUTTLE SYSTEM will be simply referred to as HME SHUTTLE.

An HME Filter is disclosed having an integral housing that improves physiological gas flow characteristics delivered in a patient's ventilator circuit. This is accomplished by using a minimalist approach eliminating components at the circuit "Y" connector. It maintains a closed circuit gas flow whether an internal filter material is or is not engaged and with or without a nebulizer aerosolizing medications. When an HME filter is desirable for optimal patient care, the HME SHUTTLE will continue to maintain the same closed circuit gas flow during the HME filter materials insertion into the HME SHUTTLE, throughout the course of the HME filter's use in the closed gas flow circuit and during the HME filter materials removal from the HME SHUTTLE. The placement for optimal patient care is to be located between the connection of inhalation and exhalation sides of mechanical ventilator circuit and endotracheal tube of an intubated patient. In addition to the HME SHUTTLE primary utility of functioning with or without an HME filter, it also accommodates the docking port for the use of a nebulizer external to this device's specification.

A novel HME SHUTTLE SYSTEM is disclosed providing the following benefits and features:

1. Ventilation device to patient's respiratory perimeters constantly maintained (i.e.: FIO2, VT, RR, PEEP).
2. May be used with standard ventilation device's heated aerosol humidification as required by an individual's own pulmonary status (use of HME Shuttle only, no HME Filter).
3. Greater ease of ventilation device circuit setup due to less circuit parts.
4. Less ventilation device circuit deadscape due to the combining of ventilator circuit "Y" connector, HME filter, HME bypass units and nebulizer "T" adapter.
5. More cost saving to medical facility than current methods (use of fewer ventilation device circuit parts and fewer HME filters).
6. Facilitates in the use of and maximizes inline nebulizer therapies by placing HME Shuttle in "Open Mode" minimizing resistance to aerosol flow.
7. Facilities in the removal of patient's respiratory track secretions when placing HME Shuttle in "Open Mode" preventing direct HME filter contamination should secretion move around a suction catheter.
8. Lowers a patient's peak airway pressure during suctioning when placing HME Shuttle in "Open Mode" preventing direct HME filter contamination of any secretion that might move around a suction catheter.
9. Less irritation to a patient's airway by requiring both fewer and decreased movements of ET tube during HME filter removal or replacement.
10. Decreases the probability of a patient developing a Ventilator Acquired Pneumonia from external environmental sources.
11. Lowers the potential risk of exposure to a patient's care giver from a ventilated patient's own airway secretions or other contaminated aerosol particles escaping into the environment.

DESCRIPTION OF THE DRAWINGS

For a more complete understanding of the present invention and the advantages thereof, reference is now made to the following description taken in conjunction with the accompanying Drawings in which

FIG. 1 is one complete HME SHUTTLE, including both Housing Unit (FIG. 4) and Filter Unit (FIG. 5) [as shown: Closed Mode FIG. 1(A)]. Internal HME Filter is not shown; Nebulizer docking port is not shown.

FIG. 2 is proposed placement of HME SHUTTLE device between ventilation device circuit and patient's endotracheal tube for maximum benefit.

FIG. 3 is exploded schematic of Housing Unit and Filter Unit.

FIG. 4 is a schematic of Housing Unit proper before permanent Filter Unit insertion, showing gas flow in and out of an HME SHUTTLE Housing Unit.

FIG. 5 is a schematic of the Filter Unit proper before permanent insertion into Housing Unit.

FIG. 6 is exploded schematic of HME SHUTTLE Filter Matrix and HME SHUTTLE Filter Sheath, and shows a schematic of the traditional material that creates the HME SHUTTLE Filter Matrix, and also shows a schematic of an HME SHUTTLE Filter Sheath with openings at each end, corresponding to those of a Filter Unit used in an HME SHUTTLE device.

FIG. 7 is a schematic of a gas flow in and out of the HME SHUTTLE Filter when inserted into the HME SHUTTLE.

FIG. 8 is the placement of one complete HME SHUTTLE Filter shown inside a Filter Unit of an HME SHUTTLE device.

FIG. 9 is exposed schematic of Housing Unit docking port and Docking Ball Valve.

FIG. 10 is a schematic of Housing Unit docking port proper before permanent Docking Ball Valve insertion.

FIG. 11 is a schematic of Docking Ball Valve before permanent insertion into Housing Unit docking port.

FIG. 12 is a schematic of Docking Ball Valve placement and external safety cap on docking port with no extended nebulizer attached (no Docking Ball Valve displacement).

FIG. 13 is a schematic of Docking Ball Valve closed in docking port before external nebulizer insertion, with the Filter Unit open.

FIG. 14 is a schematic of Docking Ball Valve open during insertion and full operation of external nebulizer, full Docking Ball deflection noted.

FIG. 15 is a schematic of an alternative embodiment (top, perspective view), showing an HME SHUTTLE (No. 62) without a docking port for a nebulizer in the housing (No. 64).

FIG. 16 is a schematic of an alternative embodiment (bottom, perspective view), showing an HME SHUTTLE (No. 62) without a docking port for a nebulizer in the housing (No. 64).

FIG. 17 is a schematic of a second alternative embodiment (top, perspective view), showing an HME SHUTTLE (No. 72) which has a housing (No. 74) which does not include a docking containment area for a nebulizer.

FIG. 18 is a schematic of a second alternative embodiment (bottom, perspective view), showing an HME SHUTTLE (No. 72) which has a housing (No. 74) which does not include a docking containment area for a nebulizer.

DETAILED DESCRIPTION OF THE INVENTION

The HME SHUTTLE for optimal patient benefit is to be placed between a ventilator circuit and patient's endotracheal tube once a patient is intubated.

The HME SHUTTLE is designed to accommodate the use of one single patient use disposable HME Filter (FIG. 7) manufactured specifically for this device. However, the insertion of an HME Filter is not mandatory to maintain proper HME SHUTTLE function.

Figure 1:
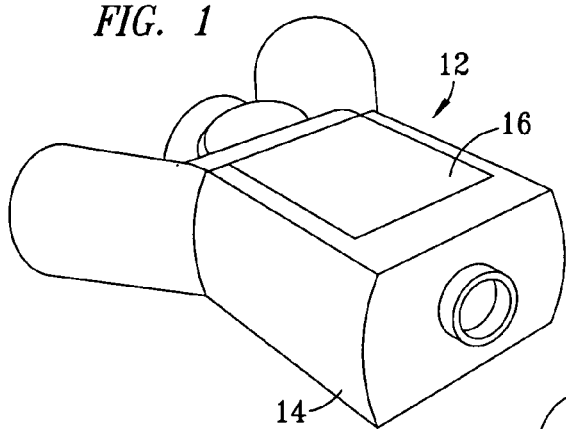
FIGS. 1 through 18 show various aspects for an HME SHUTTLE SYSTEM device made according to the present invention, as set forth below.
Figure 1A:
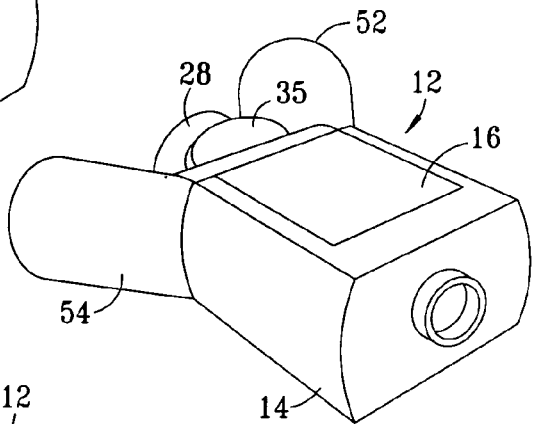
FIG. 1(A) is a schematic of complete HME SHUTTLE in the Closed Mode.
Figure 1B:
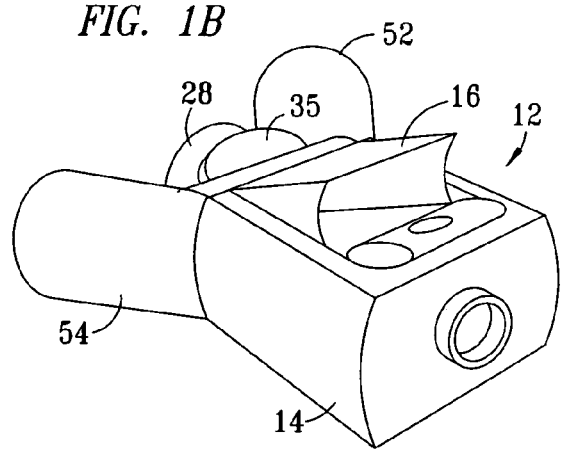
FIG. 1(B) is a schematic of a complete HME SHUTTLE in the Open Mode. (Drawing does not show HME Filter.)
Figure 1C:
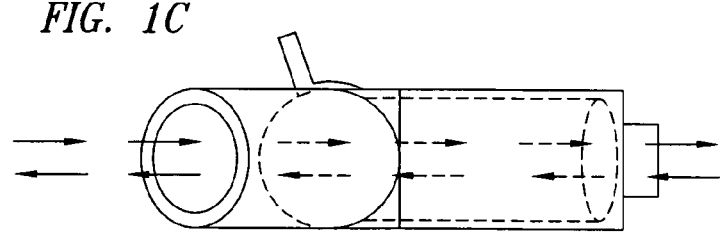
FIG. 1(C) is a schematic of a complete HME SHUTTLE, shown in Open Mode gas flow.
Figure 1D:
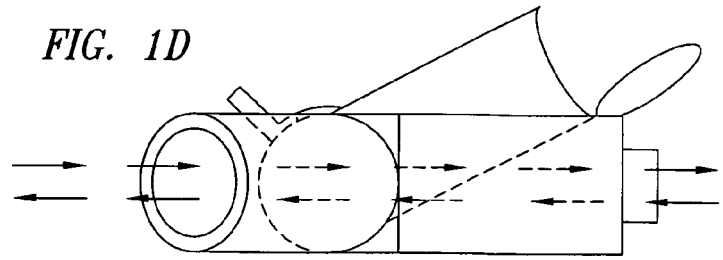
FIG. 1(D) is a schematic of a complete HME SHUTTLE, shown in Closed Mode gas flow.
Figure 2:
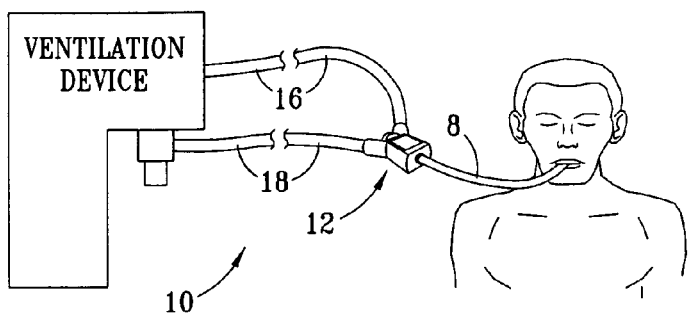
Figure 3:
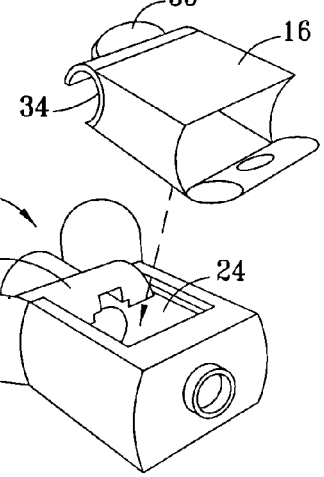

This option creates the HME SHUTTLE's duel operation modes: (1) "Open Mode" (FIG. 1B) when a medical gas passes freely through the HME SHUTTLE from the mechanical ventilator's circuit to the patient during inhalation bypassing the HME Filter and during exhalation, gases pass from patient through the HME SHUTTLE to ventilator's circuit bypassing the HME Filter. Or, (2) "Closed Mode" (FIG. 1A) when a medical gas passes through the HME SHUTTLE, including its HME Filter from the mechanical ventilator's circuit to the patient during inhalation and during exhalation gases pass from the patient through to the HME SHUTTLE, including the HME Filter, then mechanical ventilator's circuit.

"Open Mode" (FIG. 1B) operation is desirable during the times when an HME SHUTTLE Filter is being inserted or being changed. This mode also permits the HME SHUTTLE to operate fully when medication is being nebulized (FIG. 12B) requiring a filter bypass. When a patient's respiratory status changes to one requiring traditional humidification (sterile water heated to vapor phase) the HME SHUTTLE may still be utilize without the use of a HME Filter in the Filter Unit. During this period, a closed circuit gas flow will be maintained through the use of appropriate pressure seals located on the inside of the HME SHUTTLE Housing Unit Well (FIG. 4A) and corresponding appropriate pressure seals located on the outside of the HME SHUTTLE Filter Unit walls (FIG. 5B).

Figure 4:
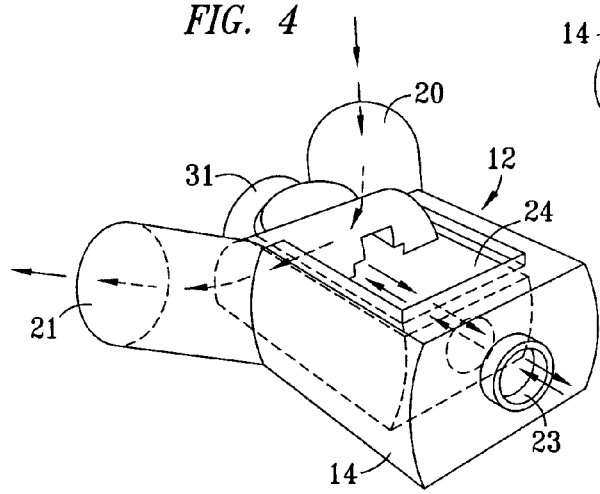
Figure 4A:
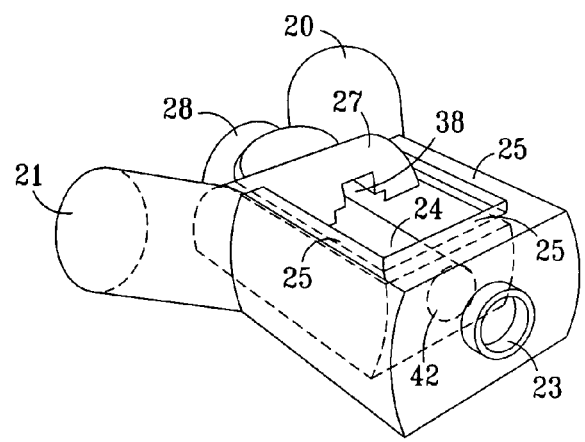
FIG. 4(A) is a schematic of pressure seal placement in the HME SHUTTLE Housing Unit.
Figure 7:
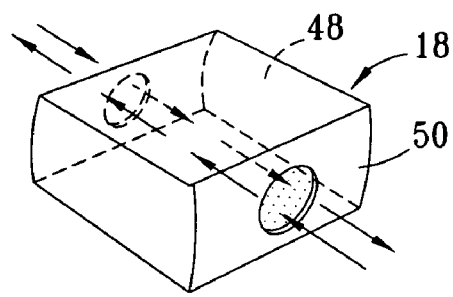
Figure 8:
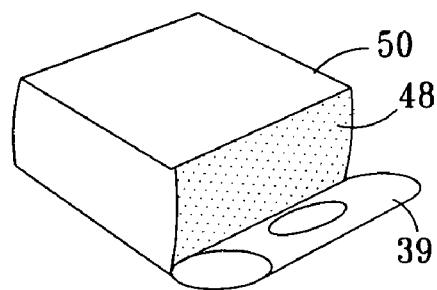

"Closed Mode" (FIG. 1A) operation requires the use of an HME SHUTTLE Filter (FIG. 7). Using a sterile technique meeting medical standards, one HME SHUTTLE Filter will be inserted inside the Filter Unit during an "Open Mode" (FIG. 1B) position. During this period, a closed circuit gas flow will be maintained through the use of appropriate pressure seals located on the inside of the HME SHUTTLE Housing Unit well (FIG. 4A) and corresponding appropriate pressure seals located on the outside of the HME Filter Unit walls (FIG. 5B). Once inserted, the HME Filter Unit is to be closed into the HME SHUTTLE Housing (FIG. 4). Again, a closed circuit gas flow will be maintained through the use of appropriate pressure seals located on the inside of the HME SHUTTLE Housing Unit wells (FIG. 4A) and corresponding appropriate pressure seals located on the outside of the HME Filter Unit walls (FIG. 5B).

When it is time for removal of a used HME SHUTTLE Filter, the procedure will be in the reverse order used for HME Filter insertion as described above. The used filter will be removed while using proven medical standards in sterile techniques to be disposed of properly and replaced with a new HME SHUTTLE filter.

It is through the use of these pressure seals (FIG. 4A), (FIG. 5B), that permit the HME SHUTTLE to maintain a closed circuit gas flow during all phases of this device's operation.

As the gas flow passes through the actual HME SHUTTLE Filter held in the HME SHUTTLE proper, the medical gas will be filtered of unwanted pathogens. In addition, the filter will be heated by the patient's own exhaled air, thereby warming the new inhaled gas it passes through the filter on its way to the patient. Humidification will also be added in the same manner by adding exhaled humidity to the filter and then rebreathing it again as the new inhaled gas passes through the filter on its way to the patient.

Figure 9:
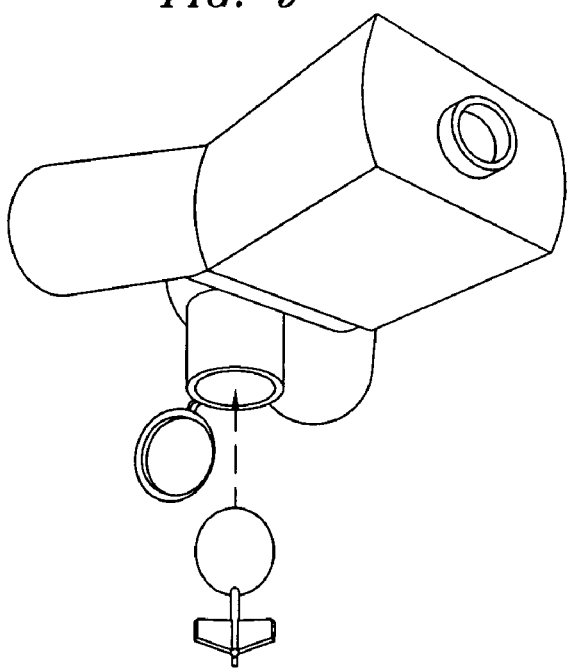

The inclusion of a nebulizer docking port (FIG. 9) on the surface opposite from the Filter Unit and located between the inspiratory and expiratory sides of the ventilator circuit connection and directly opposite of the adapter for patient's endotracheal tube permits the connection of a nebulizer external to this device for the aerosolization of medications when required for patient care. Again, a continuous closed gas flow will be maintained at this aspect of the HME SHUTTLE by a nebulizer itself when in use, or the docking port's self-sealing Docking Ball/internal docking boot interface and external safety cap when a nebulizer is not required.

The HME SHUTTLE SYSTEM consists of four primary components. However, individual components may not be necessary for each configuration mode of operation.

The four primary components are: Housing Unit FIG. 4, Filter Unit FIG. 5, HME SHUTTLE Filter FIG. 7 and Docking Ball Valve FIG. 11.

Figure 5:
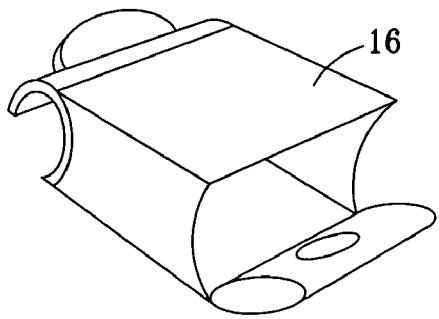
Figure 5A:
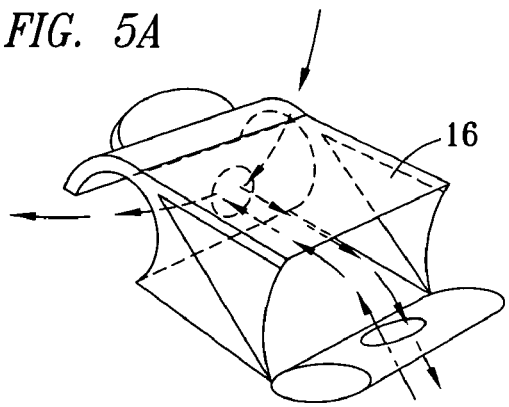
FIG. 5(A) is a schematic of a gas flow in and out of a Filter Unit.
Figure 5B:
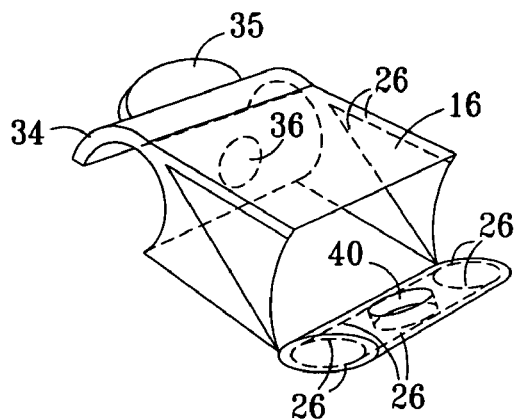
FIG. 5(B) is a schematic of placement on an HME Filter Unit for pressure seals.
Figure 11:
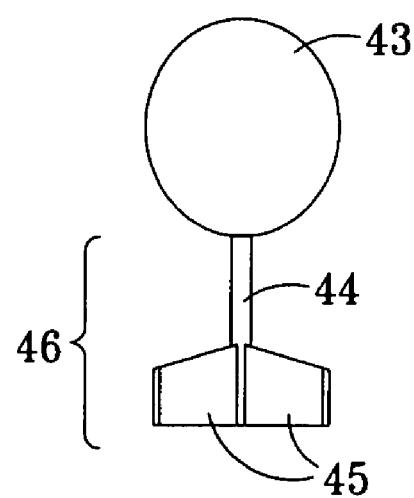

Housing Unit, FIG. 4
- The Housing Unit FIG. 4 acts as the primary structural component of the HME SHUTTLE to which all other parts function with.
- It interfaces with ventilator and patient's gas circuit by inspiratory gas flow opening (No. 20), expiratory gas flow opening (No. 21) and patient's endotracheal tube opening (No. 23).
- It contains the Filter Unit FIG. 5.
- It contains the Docking Ball Valve FIG. 11.
- It functions as the gas flow routing channel through its internal pathways to direct all inhaled gas flow through the ventilator's patient circuit inspiratory side to the patient's endotracheal tube and remove exhaled gas from the patient's endotracheal tube to the ventilator's patient circuit expiratory side, FIG. 4.
- The gas flow will pass through the Housing Unit by:
    - Closed Mode: Where a HME Filter FIG. 7 is inserted in the Filter Unit FIG. 5 and manually closed into the Housing Unit Well (No. 24) permitting the gas flow to pass through the Housing Unit, Filter Unit and HME SHUTTLE Filter.
    - or
    - Open Mode: (Operation for long duration.) Where a HME Filter FIG. 7 is not inserted in the Filter Unit FIG. 5 however still manually closed into the Housing Unit Well (No. 24) permitting the gas flow to pass through both Housing and filter Unit without filter. (Operation for short duration.) When an HME Filter FIG. 7 is not inserted in the Filter Unit FIG. 5 and not closed into the Housing Unit Well (No. 24) permitting the gas flow to pass through the Housing Unit and under Filter Unit without HME filter.
- Gas flow integrity will be maintained by using a closed circuit approach.
- Appropriate pressure seals FIG. 4(A) (No. 25) will be located on the inner walls of the Housing Unit Well (No. 24) and corresponds to matching pressure seals of the Filter Unit outer wall (No. 26).
- Use of these pressure seals (No. 25), (No. 26), will maintain this "Closed Circuit" gas flow for the HME SHUTTLE to operate in either Closed Mode or Open Mode.
- The pivot junction (No. 27) will be the permanent connection for the Filter Unit to the Housing Unit during HME SHUTTLE'S final assembly.
- The pivot junction (No. 27) will permit the Filter Unit to "shuttle" between the Open and Closed Modes of operation.
- The pivot junction (No. 27) will be located between the inhaled gas opening (No. 20) and exhaled gas opening (No. 21).
- The area located between the inhaled gas opening (No. 20), pivot junction (No. 27) and exhaled gas opening (No. 2) will accommodate the docking contained area (No. 28) for the nebulizer docking port housing (No. 29) and Docking Ball Valve FIG. 11.
- Inside the docking port housing (No. 29) will contain the Docking Ball Valve boot (No. 30).
- The Docking Ball Valve boot (No. 30) will secure the Docking Ball Valve FIG. 11 from any free movement once inserted permanently into the docking port (No. 31) and assure the Docking Ball Valve maintains an airtight seal with no external nebulizer attachment.
- A docking port safety cap (No. 32) permanently attached to the docking port nebulizer interface (No. 33) may be opened when a nebulizer is inserted or closed when a nebulizer is removed.

HME SHUTTLE (No. 62) and (No. 72) may be used with nebulizers externally connected to gas flow inhalation tubes.

Filter Unit FIG. 5
- The Filter Unit FIG. 5 acts as the HME (Heat Moisture Exchanger) Filter FIG. 7 Housing Chamber.
- On Final HME SHUTTLE assembly, the Filter Unit becomes a permanently fixed component operating inside the Housing Unit well (No. 24) and in conjunction with the Housing Unit FIG. 4.
- The permanent connection will be made with a tension clip (No. 34) to the pivot junction (No. 27) located on the Housing Unit between the inhaled gas opening (No. 20) and exhaled gas opening (No. 21).
- The pivot junction interface enables the Filter Unit to "shuttle" between the Open and Closed Modes of operation.
- An opening assist tab (No. 35) will be located on the tension clip (No. 34) to facilitate the user's "shuttling" the Filter Unit between Closed to Open Mode, short duration.
- A pressure seal will be created between the pivot junction (No. 27) and tension clip (No. 34) creating a closed circuit on this surface.
- The tension clip (No. 34) will have an opening (No. 36) that a lines with those located on the HME Filter Sheath opening (No. 37) and Housing Unit opening (No. 38).
- A spring-hinged flap (No. 39) will be located on the surface opposite of the tension clip (No. 34).

Figure 5C:
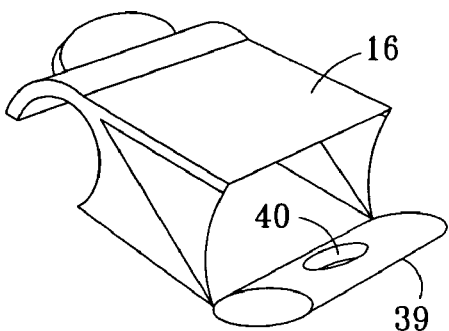
FIG. 5(C) is a schematic of Filter Unit door and tension hinge in Open mode.
Figure 5D:
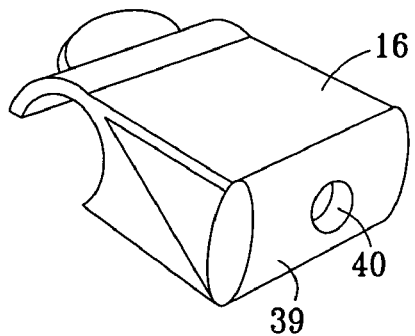
FIG. 5(D) is a schematic of Filter Unit door and tension hinge in Closed mode.

This spring-hinged will automatically open FIG. 5C during Open Mode of operation, short duration and close automatically FIG. 5D during Closed Mode of operation or Open Mode of operation, long duration.

The spring-hinged flap (No. 39) will have an opening (No. 40) that alines with those located on the HME Filter Sheath opening (No. 41) and Housing Unit endotracheal tube opening (No. 23).

A pressure seal will be created between the spring-hinged flap (No. 39) and endotracheal tube aspect (No. 42) of the Housing Unit Well creating a closed circuit on the surface.

On the two lateral external wall surfaces between the tension clip (No. 34) and spring-hinged flap (No. 39) pressure seals (No. 26) will be made against the Housing Unit inner well (No. 24).

HME SHUTTLE Filter FIG. 7

Figure 6:
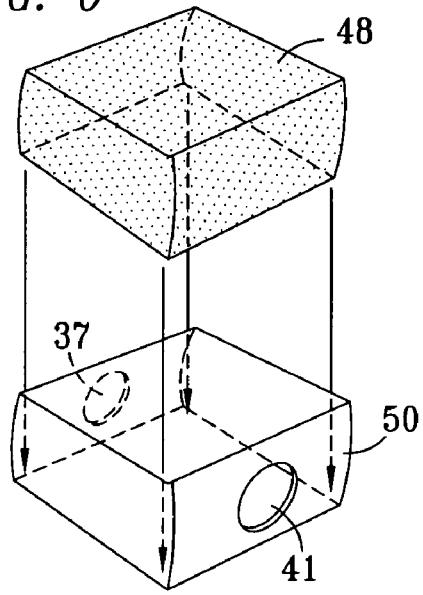

The HME Filter Matrix FIG. 6 will be composed of traditional hydroscopic material capable of retaining both heat and humidity from a patient's exhaled gas flow and releasing that heat and humidity during an inspired gas flow to a patient.

The HME Filter Matrix (No. 48) FIG. 6 shall be placed inside the HME Filter Sheath (No. 50) FIG. 6.

The Filter Matrix (No. 48) FIG. 6 shall be fashioned from one continuous piece of material.

The external dimensions of the Filter Matrix FIG. 6 are to fill the full internal volume of the Filter Sheath FIG. 6.

The shape of the Filter Matrix (No. 48) FIG. 6 maintains uniform minimum compression while inside the Filter Sheath (No. 50) FIG. 6.

The Filter Sheath FIG. 6 permanently encapsulates the Filter Matrix FIG. 6(A) to help maintain sterility during the Filter insertion into the HME Filter Unit FIG. 5.

The Filter Sheath FIG. 6 is composed of a clear material to help determine the functioning status of the enclosed Filter Matrix FIG. 6.

The Filter Sheath FIG. 6 is composed of a thin flexible material that provides maximum conformity to the internal dimensions of the HME Filter Unit FIG. 5(B).

Filter Sheath openings (No. 37), (No. 41) will be of same dimensions as that of the tension clip opening (No. 36) and spring-hinged opening (No. 40) in Filter Unit FIG. 5(B).

Filter Sheath openings (No. 37), (No. 41) will be positioned to match that of the tension clip opening (No. 36) and spring-hinged opening (No. 40) in Filter Unit FIG. 5(B).

One complete HME Filter FIG. 7 will be placed into the Filter Unit FIG. 5 for use.

Docking Ball Valve FIG. 11 and Nebulizer Docking Port (No. 31)

The nebulizer docking port (No. 31) will be located in the docking containment area (No. 28) section of an HME SHUTTLE Housing Unit FIG. 4A between the inspiratory gas flow opening (No. 20), pivot junction (No. 27) and expiratory gas flow opening (No. 21), providing nebulized aerosol.

The nebulizer docking port (No. 31) shall have an external safety cap (No. 32) to remain closed against the nebulizer interface (No. 33) with no nebulizer in use, open from the nebulizer interface (No. 33) when a nebulizer is being utilized.

A docking port nebulizer interface (No. 33) shall be the insertion point of an external nebulizer into the docking port (No. 31).

Internal diameter of docking port interface (No. 33) will provide a pressure seal to maintain a closed circuit aerosol gas flow into the HME SHUTTLE and decrease probability of the external nebulizer becoming dislodged from the docking port prematurely.

Docking port housing (No. 29) serves to secure the neck of an external nebulizer during operation and maintain a pressure seal creating a closed circuit aerosol gas flow into the HME SHUTTLE and decrease probability of the external nebulizer becoming dislodged from the docking port prematurely.

Docking port housing (No. 29) will serve as an internal operational track for the Docking Ball Valve FIG. 11 to travel during its operation and full displacement (Docking Ball Valve components moving in docking port housing).

A Docking Ball Valve boot (No. 30) is located on the interior aspect of the docking containment area (No. 28).

Figure 10:
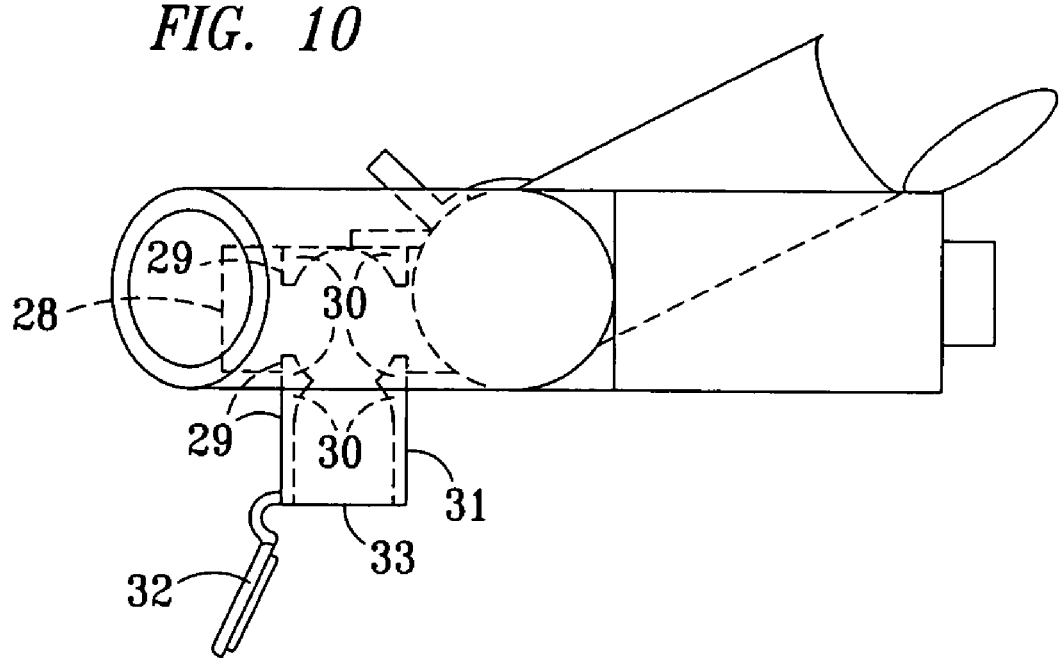

The ball boot (No. 30) provides a "cradle" for the flexible ball (No. 43) of the Docking Ball Valve FIGS. 10 and 11.

The ball boot (No. 30) serves to secure and stabilize the Docking Ball Valve FIG. 11 in a position for maintaining a closed circuit when a nebulizer is not in use and provide maximum Docking Ball Valve deflection squeezing of flexible ball (No. 43) to create an open pathway for optimal aerosol gas flow into the HME SHUTTLE when a nebulizer is in use.

A Docking Ball Valve FIG. 11 shall be inserted into the docking port (No. 31) during final assembly of an HME SHUTTLE and remain a permanent component of the HME SHUTTLE for the duration of its use.

A Docking Ball Valve FIG. 11 includes a flexible ball (No. 43) with permanently attached ball valve float (No. 46) consisting of a ball valve shaft (No. 44) and shaft fins (No. 45).

The Docking Ball Valve flexible ball (No. 43) shall be larger than the diameter of the docking port housing (No. 29) however through deflection will be able to be inserted into the ball boot (No. 30).

With an external nebulizer being inserted into the docking port, the neck of that nebulizer will make contact with the shaft fins (No. 45) and push the entire Docking Ball Valve FIG. 11 into the docking containment area (No. 28).

The Docking Ball Valve flexible ball (No. 43) will start to deflect and continue deflecting to its maximum limits as the nebulizer neck continues to push on the shaft fins (No. 45).

Figure 12:
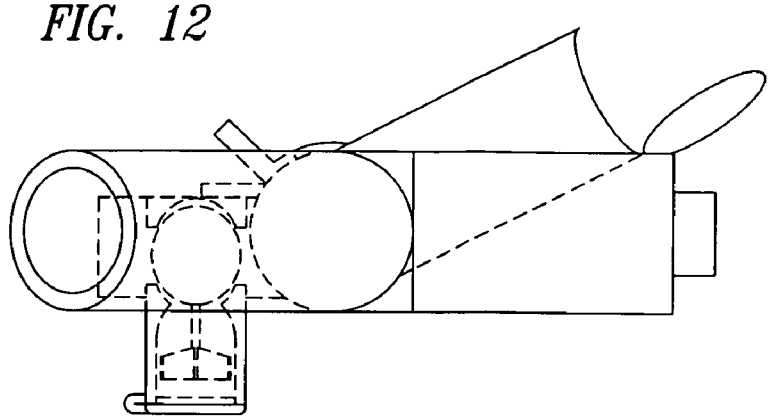
Figure 12A:
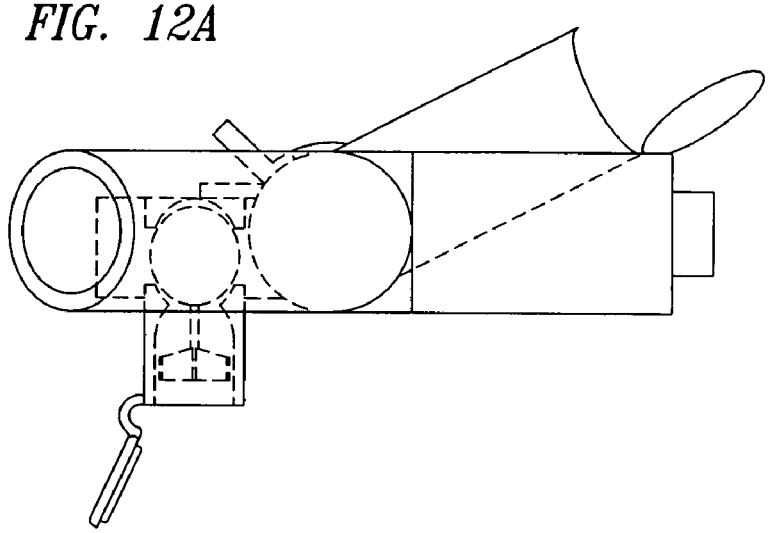
FIG. 12(A) is a schematic of docking port preparation to receive external nebulizer; safety cap open, no nebulizer, Docking Ball Valve inside Housing Unit.
Figure 12B:
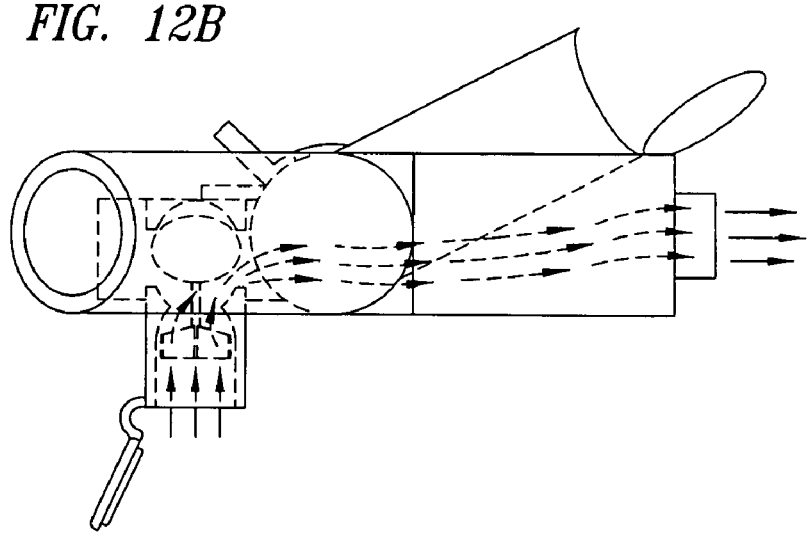
FIG. 12(B) is a schematic of open safety cap and full displacement and deflection of Docking Ball Valve in docking port, nebulizing aerosol pathway shown (no external nebulizer attached for diagram simplicity).
Figure 13:
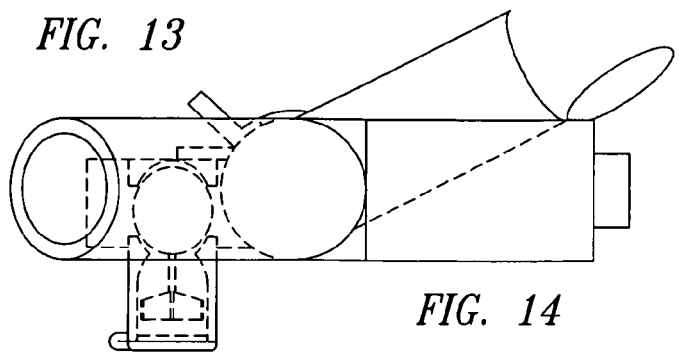
Figure 14:
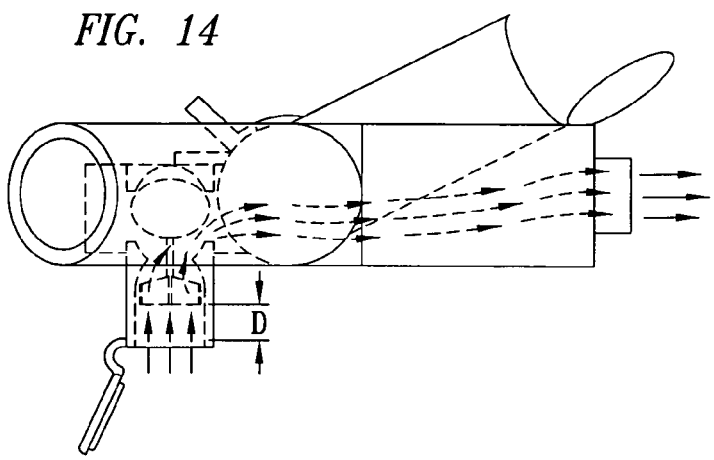
Figure 13A:
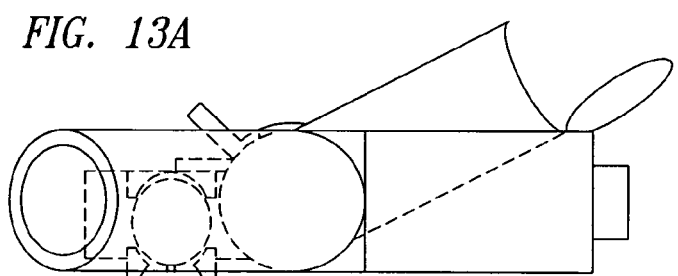
FIG. 13(A) is a schematic of position for external nebulizer placement into docking port with the safety cap open, and shows an external nebulizer before insertion into docking port.
Figure 14A:
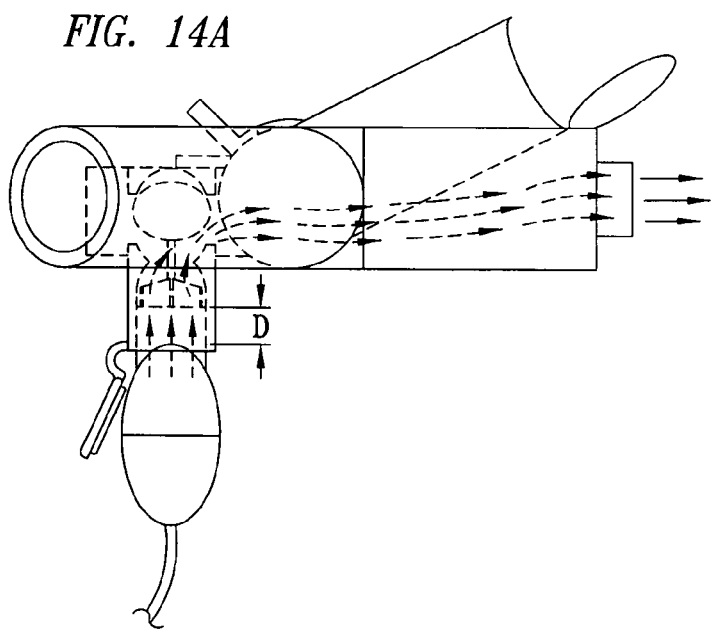
FIG. 14(A) is a schematic of position of external nebulizer placement fully inserted into docking port, and shows a docking port fully open and Docking Ball Valve fully displaced and deflected, nebulizing aerosol pathway shown, and an external nebulizer fully inserted into docking port.

Maximum deflection of the Docking Ball Valve flexible ball (No. 43) will create a passageway for nebulizer aerosol to inter and then travel through HME SHUTTLE to the patient's endotracheal tube FIG. 12B, along with gas flowing from and to the ventilation device 10.

Figure 15:
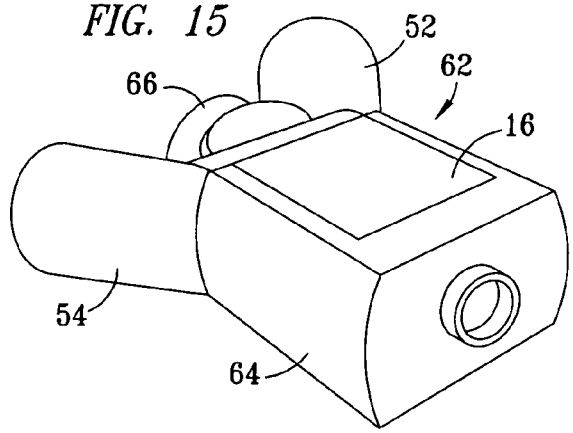
Figure 16:
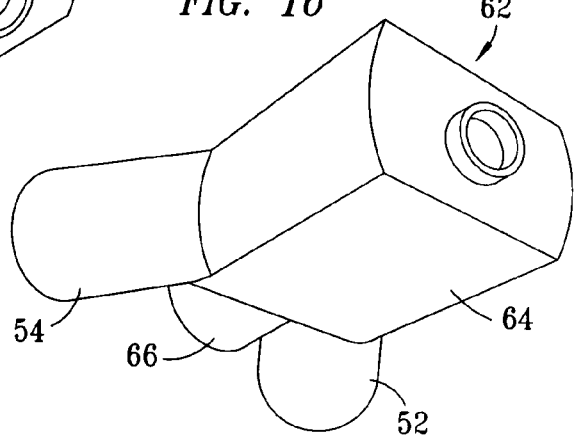

FIG. 15 (top, perspective view) and FIG. 16 (bottom perspective view), show an HME SHUTTLE 62 without a docking port for a nebulizer in the housing 64.

Figure 17:
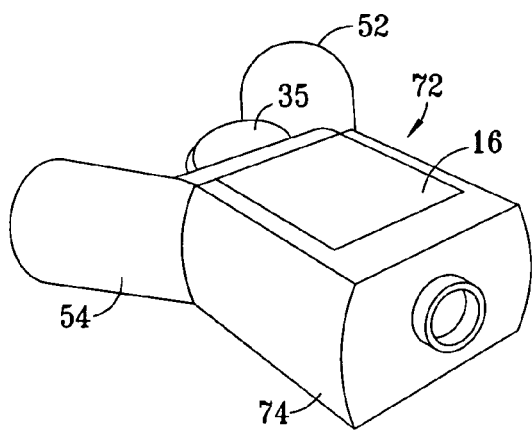
Figure 18:
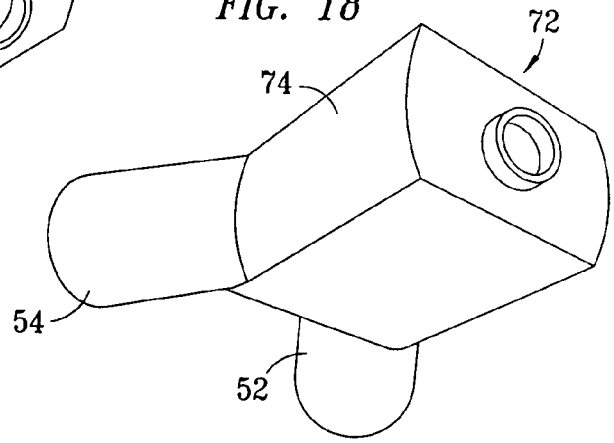

FIG. 17 (top perspective view) and FIG. 18 (bottom perspective view), show an HME SHUTTLE 72 which has a housing 74 which does not include a docking containment area for a nebulizer.

HME SHUTTLEs 62 and 72 may be used with nebulizers externally connected to gas flow inhalation tubes.

PRIMARY COMPONENT PART NUMBERS

Patient—Ventilator Interface (10)
   8 endotracheal tub
   16 inhalation tube
   18 exhalation tube
HME Shuttle (12)
Housing Unit (14)
   20 inspiratory gas flow opening
   21 expiratory gas flow opening
   23 endotracheal tube opening
   24 housing unit well/cavity
   25 pressure seals, inner well
   27 pivot junction
   28 docking containment area
   29 docking port housing
   30 docking ball valve boot
   31 docking port
   32 docking port safety cap
   33 docking port nebulizer interface
   38 pivot junction opening
   52 tube connectors having openings (No. 20) and (No. 21)
   54 tube connectors having openings (No. 20) and (No. 21)
Filter Unit (16)
   26 pressure seals, outer wall
   34 tension clip
   35 opening assist tab
   36 tension clip opening
   39 spring-hinged flap
   40 spring-hinged flap opening
   42 endotracheal tube aspect
HME Filter (18)
   37 filter sheath opening, tension clip side
   41 filter sheath opening, endotracheal side
   48 filter material (may be sponge material)
   50 filter sheath (cover)
Nebulizer Docking Port (31)
   43 flexible ball
   44 ball shaft
   45 ball shaft fins
   46 ball valve float Although the preferred embodiment has been described in detail, it should be understood that various changes, substitutions and alterations can be made therein without departing from the spirit and scope of the invention as defined by the appended claims.

What is claimed is:

1. An HME shuttle comprising:
a housing unit having an inspiratory gas flow opening, an expiratory gas flow opening, an endotracheal tube opening, and a housing unit cavity;
a filter unit for fitting within said housing unit cavity and sealing engaging within an opening of said housing unit cavity, wherein said filter unit is movably secured to said housing unit for moving between a first position and a second position, and said filter unit includes an open space for receiving an HME filter;
wherein said filter unit when in said first position sealing engages with said opening of said housing unit cavity and is disposed for passing air flow through said HME filter in passing between said endotracheal tube opening and respective ones of said inspiratory gas flow opening and said expiratory gas flow opening; and
wherein said filter unit when in said second position sealing engages with said opening of said housing unit cavity and is disposed for passing air flow aside of said HME filter in passing between said endotracheal tube opening and respective ones of said inspiratory gas flow opening and said expiratory gas flow opening, and an opening in said filter unit is disposed for removing said HME filter.

2. The HME shuttle according to claim 1, wherein a docking containment area is provided having a docking port for receiving a nebulizer.

3. The HME shuttle according to claim 2, wherein said docking port comprises a valve having a flexible seal ball.

4. The HME shuttle according to claim 1, wherein said HME filter comprises a filter element disposed within a flexible sheath.

* * * * *